(12) United States Patent
Hanebuchi et al.

(10) Patent No.: US 8,220,924 B2
(45) Date of Patent: Jul. 17, 2012

(54) APPARATUS AND METHOD FOR GENERATING TWO-DIMENSIONAL IMAGE OF OBJECT USING OPTICAL COHERENCE TOMOGRAPHY (OCT) OPTICAL SYSTEM

(75) Inventors: Masaaki Hanebuchi, Aichi (JP);
Yasuhiro Furuuchi, Aichi (JP);
Norimasa Satake, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 13/048,959

(22) Filed: Mar. 16, 2011

(65) Prior Publication Data

US 2011/0228221 A1 Sep. 22, 2011

(30) Foreign Application Priority Data

Mar. 16, 2010 (JP) ................................. 2010-059439
Mar. 1, 2011 (JP) ................................. 2011-044485

(51) Int. Cl.
*A61B 3/00* (2006.01)
*A61B 3/10* (2006.01)

(52) U.S. Cl. ...................................... 351/205; 351/200

(58) Field of Classification Search .................. 351/200, 351/205, 206, 208, 222
See application file for complete search history.

(56) References Cited

U.S. PATENT DOCUMENTS

| | | | |
|---|---|---|---|
| 5,975,697 A | 11/1999 | Podoleanu et al. | |
| 7,301,644 B2 | 11/2007 | Knighton et al. | |
| 7,510,282 B2 | 3/2009 | Ueno et al. | |
| 7,659,990 B2 * | 2/2010 | Knighton et al. | 356/479 |

FOREIGN PATENT DOCUMENTS

| | | |
|---|---|---|
| JP | 2008029467 | 2/2008 |
| WO | 2009033064 | 3/2009 |

* cited by examiner

*Primary Examiner* — Joseph P Martinez
*Assistant Examiner* — Brandi Thomas
(74) *Attorney, Agent, or Firm* — Lowe Hauptman Ham & Berner LLP (57) ABSTRACT

An apparatus for generating a two-dimensional image of an object using an optical coherence tomography (OCT) optical system, includes: the OCT optical system including: a light source; a splitter for splitting light emitted from the light source into a measurement optical path and a reference optical path; a scanner arranged in the measurement optical path for scanning the object in at least one of XY directions with the split light; and a detector for detecting a spectrum of combined light of the split light from the measurement optical path reflected on the object and the split light from the reference optical path each XY position of the light on the object, and a processor for generating the two-dimensional image of the object in the XY directions by converting the number of zero cross points of an interference signal contained in the spectrum at each XY position into a luminance value.

11 Claims, 10 Drawing Sheets

APPARATUS AND METHOD FOR GENERATING TWO-DIMENSIONAL IMAGE OF OBJECT USING OPTICAL COHERENCE TOMOGRAPHY (OCT) OPTICAL SYSTEM

CROSS-REFERENCE TO RELATED APPLICATION

This application is based on Japanese Patent Application Nos. 2010-059439 filed Mar. 16, 2010 and 2011-044485 filed Mar. 1, 2011 with the Japan Patent Office, the entire contents of which are hereby incorporated by reference.

BACKGROUND

1. Technical Field

An aspect of the invention is related to an apparatus and a method for generating a two-dimensional image of an object using an optical coherence tomography (OCT) optical system.

2. Related Art

There is known an optical tomographic image photographing apparatus (Optical Coherence Tomography: OCT) which has an interference optical system and photographs a tomographic image of an object. The optical interference optical system of this apparatus splits a light flux emitted from a light source into a measurement light flux and a reference light flux. This optical interference optical system then guides the measurement light flux to an object, while guiding the reference light flux to a reference optical system. Subsequently, the optical interference optical system combines the measurement light flux, reflected on the object, with the reference light flux, to obtain interference light, and thereafter makes a light receiving device receive this interference light. This apparatus is used for, for example, obtaining a tomographic image of a living body such as an eyeball or skin.

An apparatus of related art is an apparatus in which either a scanning laser ophthalmoscope (SLO) or an infrared camera and an interference optical system are combined (refer to JP-A-2008-29467). An examiner decides a position for obtaining a tomographic image while observing a front image of an object.

In the case where the SLO or the infrared camera is provided in the apparatus, the number of optical systems increases. This brings about cost increase.

Also, recently, a method for obtaining a front image without using such a configuration is disclosed (refer to U.S. Pat. No. 7,301,644). In this method, the front image is obtained by scanning an object two-dimensionally by a measurement light flux and integrating a spectral intensity of an interference signal obtained from a light receiving device on each point in X-Y directions.

SUMMARY

In an aspect of the invention, a two-dimensional image of an object in X-Y directions is generated by use of an optical spectrum detected by an OCT.

An aspect of the invention is configured as follows.

An apparatus for generating a two-dimensional image of an object using an optical coherence tomography (OCT) optical system, includes: the OCT optical system including: a light source; a splitter for splitting light emitted from the light source into a measurement optical path and a reference optical path; a scanner that is arranged in the measurement optical path for scanning the object in at least one of X and Y directions with the split light; and a detector configured to detect a spectrum of combined light of the split light from the measurement optical path reflected on the object and the split light from the reference optical path with respect to each of X and Y positions of the light on the object, and a processor configured to generate the two-dimensional image of the object in the X and Y directions by converting the number of zero cross points of an interference signal contained in the spectrum at each of the X and Y positions into a luminance value.

BRIEF DESCRIPTION OF THE DRAWINGS

The foregoing and other objects, features, aspects and advantages of the invention will become more apparent from the following detailed description when taken in conjunction with the accompanying drawings, in which.

DESCRIPTION OF EMBODIMENTS

Preferred embodiments of the present invention will be described below with reference to the accompanying drawings, in which like reference characters designate similar or identical parts throughout the several views thereof.

Figure 1:
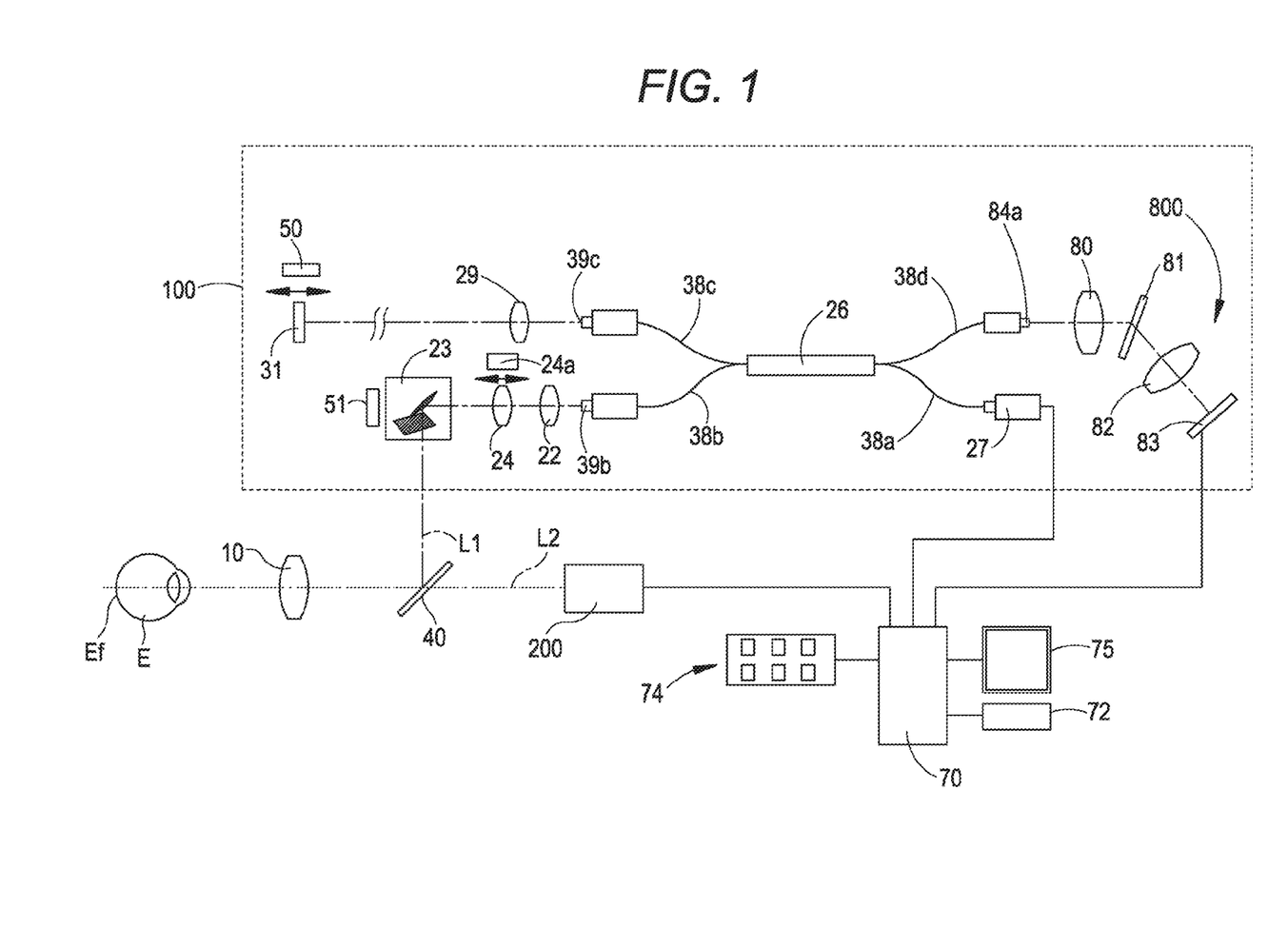
FIG. 1 illustrates an optical system and a control system of an optical tomographic image photographing apparatus of an embodiment of the invention.

An embodiment in accordance with an aspect of the invention will be described based on the drawings. FIG. 1 illustrates an optical system and a control system in an optical tomographic image photographing apparatus of an embodiment of the invention. In the embodiment, a fundus photographing apparatus as an example of an ophthalmic photographing apparatus will be described. It is to be noted that in the embodiment, a description is given with a depth direction of an examinee's eye referred to as a Z-direction (direction of optical axis L1), a horizontal direction referred to as an X-direction, and a vertical direction referred to as a Y-direction.

As shown in FIG. 1, the optical system of this ophthalmic photographing apparatus is broadly divided into an interference optical system (hereinafter referred to as OCT optical system) 100 and a fixation target projecting optical system (hereinafter referred to as a projecting optical system) 200.

The OCT optical system 100 serves to obtain a tomographic image of a fundus of an examinee's eye noninvasively by use of an optical interference technique. Meanwhile, the projecting optical system 200 serves to project a fixation target to the fundus of the examinee's eye. It is to be noted that the OCT optical system 100 and the projecting optical system 200 are incorporated in a housing (not illustrated). This housing is three-dimensionally moved with respect to an examiner's eye E by a known (manual or electrically-powered) movement mechanism for alignment. Also, this housing may be a handy-type housing.

A dichroic mirror 40 is used as an optical path splitting member for splitting an optical path into an optical path of the OCT optical system 100 and an optical path of the projecting optical system 200. The dichroic mirror 40 has a characteristic of reflecting measurement light used in the OCT optical system 100, while transmitting visible light used in the projecting optical system 200. The dichroic mirror 40 also makes an optical axis L1 of the OCT optical system 100 and an optical axis L2 of the projecting optical system 200 be the same axial.

The OCT optical system 100 is provided in a reflecting direction of the dichroic mirror 40. This OCT optical system 100 splits a light flux emitted from a light source into a measurement light flux and a reference light flux. Further, the OCT optical system 100 guides the measurement light flux to a fundus Ef of the examinee's eye, while guiding the reference light flux to a reference optical system. Subsequently, the OCT optical system 100 makes a light receiving device receive interference light obtained by combining the measurement light flux, reflected on the fundus Ef, with the reference light flux. As the OCT optical system 100 of this ophthalmic photographing apparatus, there has been used an OCT optical system of a spectral domain type. Alternatively, a swept source type (SS-OCT) optical system may also be used. This optical system detects a spectrum of the interference light by use of a wavelength-variable light source that varies a wavelength of light to be emitted.

An OCT light source 27 emits low coherent light that is used as measurement light and reference light of the OCT optical system 100. As the OCT light source 27, there is for example used a light source that emits light with a central wavelength of 880 nm and a band width of 50 nm (e.g., SLD light source). A fiber coupler 26 serves as a light splitting member as well as a light coupling member. The light emitted from the OCT light source 27 passes through an optical fiber 38a as a guiding optical path, and is thereafter split by the coupler 26 into reference light and measurement light. The measurement light travels toward the eye E via an optical fiber 38b, while the reference light travels toward a reference mirror 31 via an optical fiber 38c.

In an optical path for emitting the measurement light toward the eye E, an end 39b of the optical fiber 38b, a collimator lens 22, a focusing lens 24 and a scanning part 23 are arranged. The focusing lens 24 is movable in the optical-axis direction in line with a refraction error of the eye E for adjustment of a focus on the fundus. The scanning part 23 is capable of scanning the fundus in XY directions with the measurement light. This scanning part 23 includes two galvanometer mirrors, and is operated by driving of a scanning driving mechanism 51. The dichroic mirror 40 and an objective lens 10 serve as a light guiding optical system for guiding OCT measurement light from the OCT optical system 100 to the fundus. It is to be noted that the scanning part 23 of the embodiment appropriately adjusts a reflection angle of the measurement light by means of the two galvanometer mirrors. Hence a direction of scanning by means of the measurement light on the fundus is appropriately set. A tomographic image in any area of the fundus is thus obtained. It is to be noted that the end 39b of the optical fiber 38b is arranged in a position conjugate with the fundus of the eye E. Further, the two galvanometer mirrors of the scanning part 23 are arranged in a position substantially conjugate with a pupil of the eye E.

The galvanometer minors and the scanning driving mechanism 51 described above are used as an optical scanner (optical scanning part). The optical scanner is arranged in the optical path for the measurement light flux (measurement optical path). The optical scanner changes a traveling direction of the measurement light flux in order to scan a predetermined region of the eye in a transverse direction (XY directions) with the measurement light flux. As the optical scanner, in addition to the mirror, an acousto-optic device (AOM: Acousto-Optic Modulator) for changing a traveling (deflection) direction of light, and the like are used.

The measurement light emitted from the end 39b of the optical fiber 38b is collimated by the collimator lens 22, and thereafter reaches the scanning part 23 via the focusing lens 24. In this scanning part 23, the two galvanometer mirrors are driven, to change a reflecting direction of the measurement light. The measurement light reflected on the scanning part 23 is reflected on the dichroic minor 40, and thereafter collected in the fundus via the objective lens 10.

The measurement light reflected on the fundus passes through the objective lens 10, and is thereafter reflected on the dichroic mirror 40, to travel toward the OCT optical system 100. Further, the measurement light is incident on the end 39b of the optical fiber 38b via the two galvanometer minors of the scanning part 23, the focusing lens 24 and the collimator lens 22. The measurement light incident on the end 39b reaches an end 84a of an optical fiber 38d via the optical fiber 38b, the fiber coupler 26 and the optical fiber 38d.

Meanwhile, in an optical path for emitting reference light toward the reference minor 31 (reference optical path), an end 39c of the optical fiber 38c, a collimator lens 29 and the reference mirror 31 are arranged. The reference mirror 31 is configured to be movable in the optical-axis direction by a reference mirror driving mechanism 50. This allows the reference mirror 31 to change an optical path length of the reference light. In the configuration shown in FIG. 1, in order to adjust the optical path difference between the measurement light and the reference light, an optical-path-length varying member is provided in the reference optical path. However, the embodiment is not limited to this configuration, and the optical-path-length varying member may also be provided in the measurement optical path. In this case, for example, the collimator lens 22 and the end of the optical fiber 39b are moved in the optical-axis direction. Also, the reference optical system may be a reflective reference optical system as shown in FIG. 1 or a transmissive reference optical system.

The reference light emitted from the end 39c of the optical fiber 38c is made to be a parallel light flux by the collimator lens 29 and reflected on the reference mirror 31, and is thereafter collected by the collimator lens 29, to be incident on the end 39c of the optical fiber 38c. The reference light incident on the end 39c reaches the coupler 26 via the optical fiber 38c.

The reference light generated as described above and the fundus reflected light obtained by reflection of the measurement light on the fundus are combined in the coupler 26, to become interference light. The interference light is emitted from the end 84a through the optical fiber 38d.

A spectroscopic optical system 800 (spectrometer part) splits the interference light into each wavelength (frequency) component for obtaining an interference signal with reference to each wavelength (frequency). Thereby, the spectroscopic optical system 800 detects a spectrum of the interference light. The spectroscopic optical system 800 has a collimator lens 80, a grating (diffraction grating) 81, a condenser lens 82 and a light receiving device (detector) 83. The light receiving device 83 includes a one-dimensional device (line sensor) having the sensitivity to light with a wavelength in an infrared region.

The light emitted from the end 84a is made to be parallel light in the collimator lens 80, and thereafter split in the grating 81 into each frequency component (each wavelength component). The interference light split into each wavelength is then collected on the light receiving surface of the light receiving device 83 via the condenser lens 82. Thereby, spectrum information with interference fringes is recorded in the light receiving device 83. The spectrum information (light receiving signal) is then input into a control part 70. The control part 70 analyzes the spectrum information by use of Fourier transformation, to measure information (A-scan signal) in the depth direction of the eye.

Using the scanning part 23, the control part 70 scans the fundus in a predetermined transverse direction with the measurement light, to obtain a tomographic image. The obtained tomographic image is stored in a memory 72 connected to the control part 70. Further, the control part 70 scans two-dimensionally the fundus in the XY directions with the measurement light, to obtain a three-dimensional image of the fundus.

The projecting optical system 200 is provided in a transmitting direction of the dichroic mirror 40. This projecting optical system 200 is an optical system for fixating the examinee's eye and is preferably configured to enable changes of a fixation direction. As the projecting optical system 200, a point-like light source (for example, LED) or a liquid crystal display can be used, for example.

It is to be noted that the control part 70 is connected to a display monitor 75, and controls a display image thereof. Further, the control part 70 is connected with a memory (storing part) 72, an operating part 74 for performing a variety of operations, the scanning driving mechanism 51, the reference mirror driving mechanism 50, a driving mechanism 24a for moving the focusing lens 24 in the optical-axis direction, and the like. It is to be noted that as the monitor 75, two monitors, that is, a monitor for alignment observation and a monitor for photographed image observation, may be used or one shared monitor may naturally be used.

The overall operation of the apparatus configured as above will be described. The control part 70 processes spectral data detected by the light receiving device 83. The control part 70 then forms a tomographic image and a front image of the fundus by image processing. The tomographic image and the front image are obtained simultaneously, alternately or sequentially. That is, the spectral data is used to obtain at least either the tomographic image or the front image.

Figure 2A:
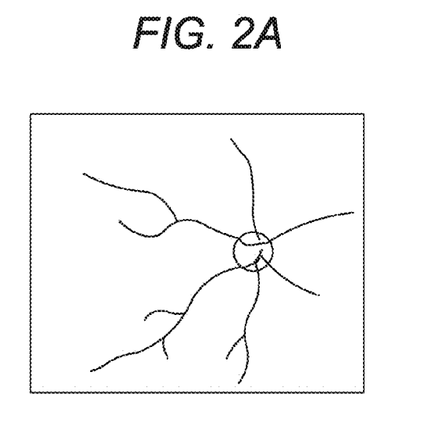
FIG. 2A illustrates a schematic view showing an obtained front image.
Figure 2B:
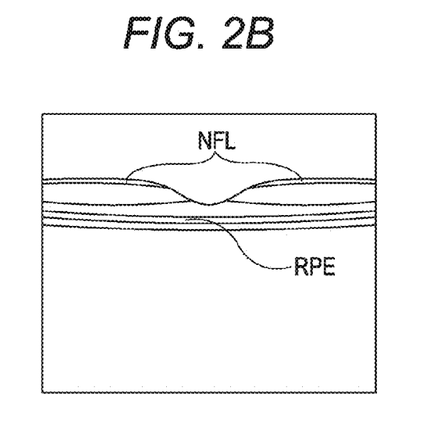
FIG. 2B illustrates a schematic view showing an obtained tomographic image.

To obtain a tomographic image, the control part 70 scans the fundus Ef in a transverse direction with the measurement light, using the scanning driving mechanism 51. The control part 70 then detects spectral data output from the light receiving device 83 with respect to each scanning position (X,Y) on the fundus. Further, the control part 70 converts an interference signal contained in the detected spectral data into a depth profile. Subsequently, the control part 70 arranges the depth profiles in a scanning direction to form a tomographic image of the fundus (refer to FIG. 2B).

The interference signal is extracted by denoising the spectral data. The interference signal is converted into the depth profile by analyzing an amplitude level of each frequency (wavenumber) of the interference signal. A representative method of the frequency analysis to be used is Fourier transformation. It is to be noted that possible examples of the scanning pattern with the measurement light are line, crossline, raster, circle and radial patterns. Also, a three-dimensional OCT image is obtained by the two-dimensional scanning with the measurement light. Also, the tomographic image may be obtained as a moving image with a predetermined frame rate or as a still image.

To obtain a front image, the control part 70 two-dimensionally scans the fundus Ef in XY directions with the measurement light, using the scanning driving mechanism 51. The control part 70 then obtains an interference signal from spectral data output from the light receiving device 83. Subsequently, the control part 70 detects the number of zero cross points in the interference signal contained in the spectrum with respect to each scanning position (X,Y) when the fundus Ef is two-dimensionally scanned in the X-Y directions with the measurement light. Based on this detection result, the control part 70 obtains a two-dimensional image of the object in the X-Y directions (refer to FIGS. 3, 4 and 5).

The interference signal based on the spectral data is converted into a luminance value by detecting the number of its zero cross points. For example, a real signal of the interference signal is Hilbert-transformed to obtain an analysis signal in which the real signal and an imaginary signal of the interference signal are added. Subsequently, based on the obtained analysis signal, a phase signal representing change in phase on each wavelength of the interference light is obtained. Finally, based on the phase signal, the number of zero cross points is detected (refer to FIG. 4). It is to be noted that this phase signal may be obtained as a signal representing change in phase on wavenumber, which is a reciprocal of the wavelength.

Figure 5:
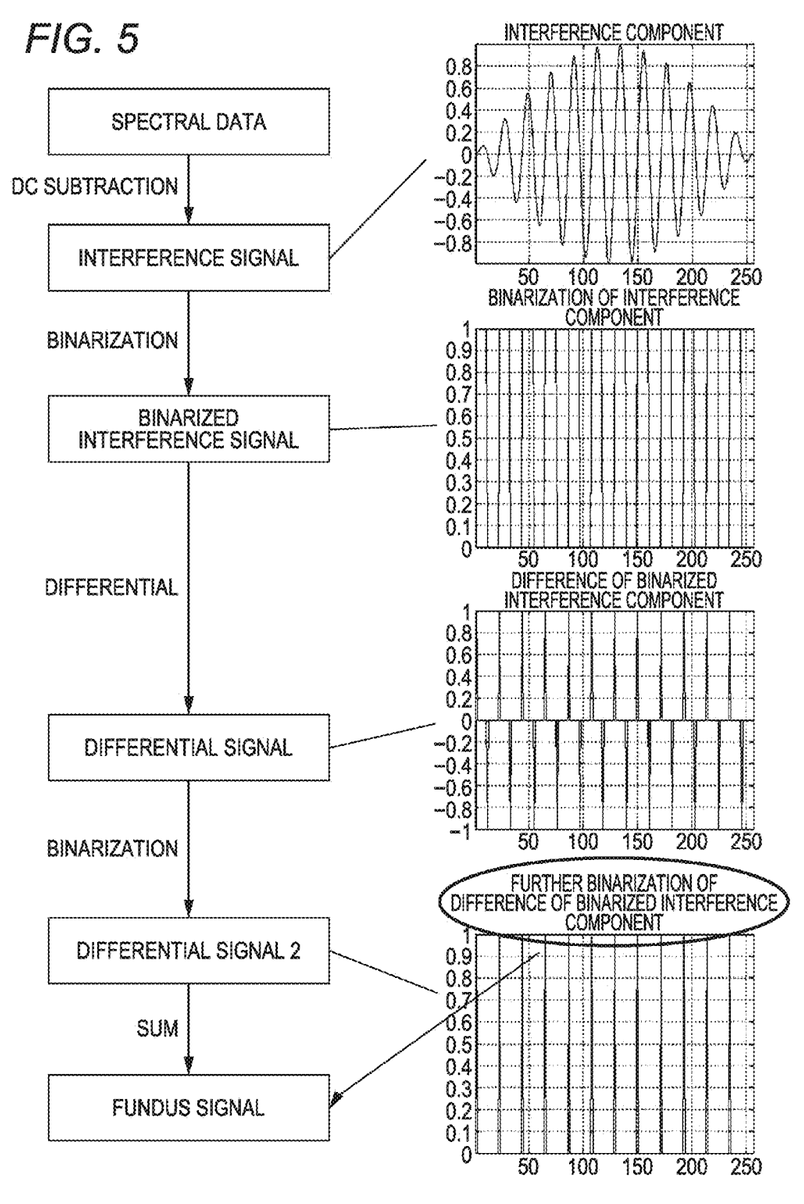
FIG. 5 illustrates a flowchart showing a second embodiment of the invention.

Also, the number of zero cross points may be detected directly from the real signal of the interference signal (refer to FIG. 5). Alternatively, an electric circuit for detecting the number of zero cross points of the interference signal may be used.

It is to be noted that the front image may be obtained in parallel with the aforementioned three-dimensional OCT image or independently. Also, the front image may be obtained as a moving image with a predetermined frame rate or as a still image. Also, when a conversion setting to a luminance value with respect to the fundus image is determined such that the luminance may be higher in a case where the number of zero cross points is higher, the fundus image to be obtained is easy to observe as an image. However, in some objects, a setting such that the luminance may be higher in a case where the number of zero cross points is lower may be preferable.

Figure 3:
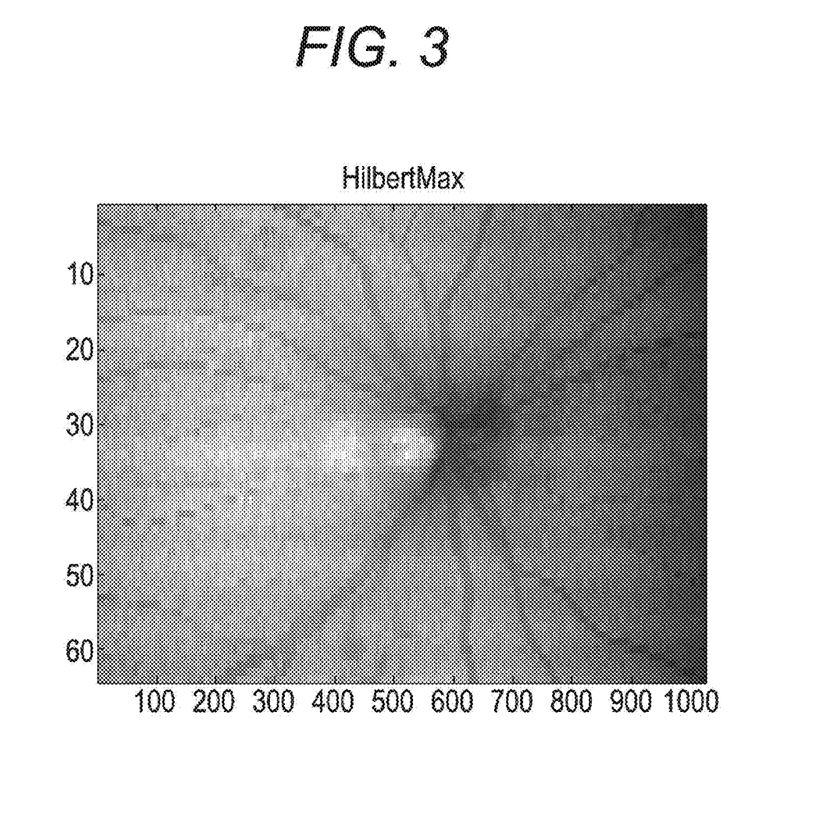
FIG. 3 illustrates a real image of a fundus front image formed based on the number of zero cross points of an interference signal.
Figure 4:
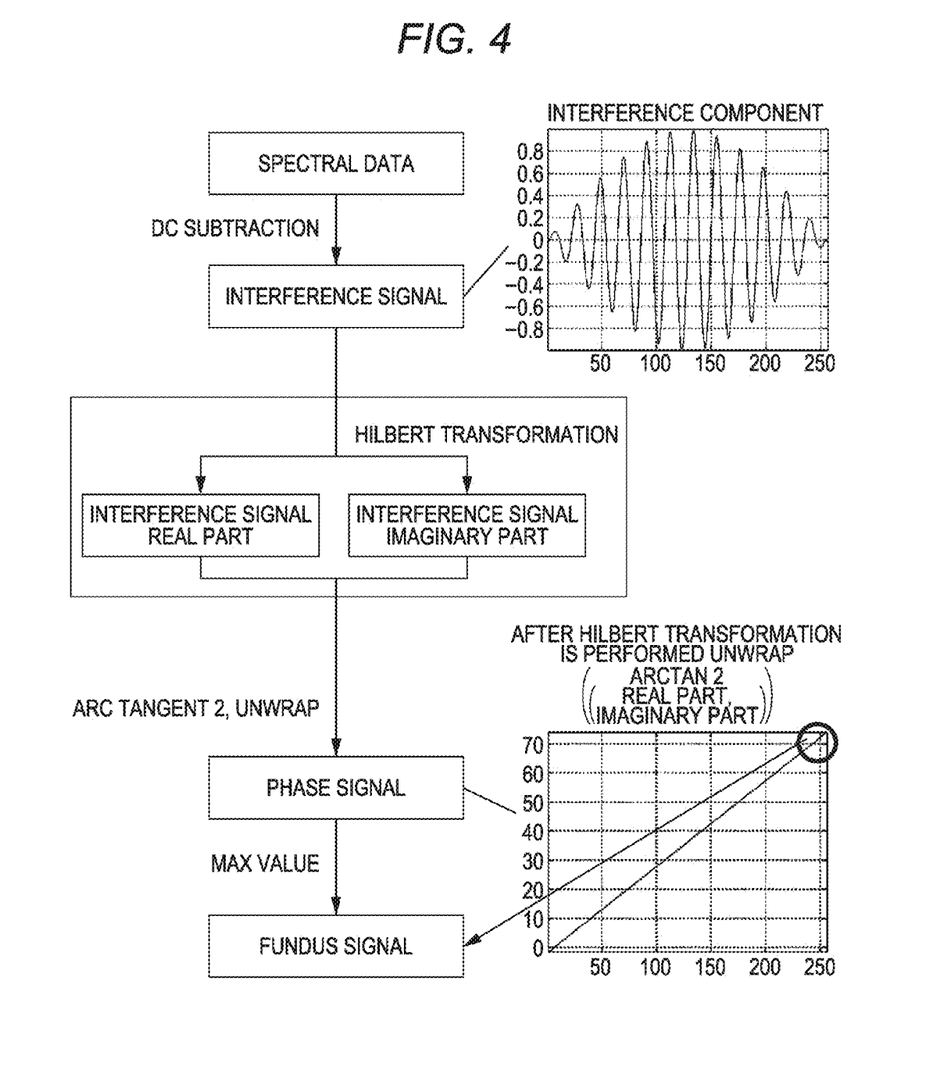
FIG. 4 illustrates a flowchart describing processing from obtaining of spectral data to conversion into a luminance value.

FIG. 3 shows a real image of a fundus front image formed by converting the number of zero cross points of an interference signal into a luminance value. FIG. 4 illustrates a flowchart describing processing from obtaining of spectral data to converting the data into a luminance value. An overview of the processing until the fundus front image is formed will first be described, and thereafter its detailed specific method will be described.

An interference signal contains each interference signal corresponding to reflected light scattered at a different depth position on the fundus. When the interference signal is regarded as a wave at the micro level, the interference signal is a collection of waves with different wavenumbers (frequencies). Here, the wavenumber of the wave has a predetermined relationship with the depth on the fundus. The wavenumber changes per depth position on the fundus.

It is to be noted that the wavenumber represents the extent of phase lead when the wave proceeds by unit length. The faster the phase lead is, the larger the wavenumber is. Conversely, the slower the phase lead is, the smaller the wavenumber is.

For example, a waveform with the slowest phase lead is formed by an interference signal corresponding to reflected light from a fundus portion closest to an optical path length conforming position (depth position corresponding to the arranging position of the reference mirror 31), at which optical path lengths of the measurement light and the reference light conform with each other. As the reflection position is further away from this closest portion, the phase lead of the interference signal is faster. For example, in a case where the optical path length conforming position is located at the front portion of the fundus, as the reflection position of the reflected light on the fundus is shallower, the interference signal represents a waveform with slower phase lead. Conversely, as the reflection position of the reflected light on the fundus is deeper, the interference signal represents a waveform with faster phase lead.

By utilizing such characteristics, an amplitude level of each frequency (wavenumber) of the interference signal is calculated. Thereby, a depth profile (A scan signal) representing a reflection intensity of the measurement light at each depth position is obtained.

On the other hand, when the interference signal is regarded as a wave at the macro level, the interference signal is dominated by reflected light from a portion having a high reflectance with respect to the measurement light. That is, an interference signal corresponding to reflected light reflected from a portion having a high reflectance has a waveform with large amplitude. On the contrary, an interference signal corresponding to reflected light reflected from a portion having a low reflectance has a waveform with relatively small amplitude. Hence, the latter interference signal is buried under the former one. Also, in a case where there are plural portions having a high reflectance along the depth direction, a waveform with large amplitude is formed by mixing plural interference signals corresponding to reflected light from the portions. Naturally, when a micro analysis is conducted by Fourier analysis or the like as described above, a waveform with small amplitude is also extracted.

Accordingly, in a case where the extent of phase lead of an interference signal is approximately calculated, the calculation result contains the extent of phase lead of a waveform with large amplitude but rarely contains the extent of phase lead of a waveform with small amplitude.

The extent of phase lead of the interference signal obtained approximately can be derived by detecting the number of zero cross points in the interference signal. In this case, the faster the phase lead is, the larger the number of zero cross points is. Conversely, the slower the phase lead is, the smaller the number of zero cross points is.

Then, when the number of zero cross points is converted into a luminance value L, the depth position at a portion having a high reflectance is expressed by luminance. In this case, difference in luminance (high/low luminance) is shown as difference in depth position at a portion having a high reflectance. By arranging the luminance L at each scanning position (X, Y) to correspond to each pixel, it is shown as image data. Accordingly, information expressing two-dimensional distribution of the depth positions at portions having a high reflectance is obtained as distribution of the luminance values (refer to FIG. 3).

FIG. 3 illustrates an image in a case where the optical path length conforming position is located at the front portion of the fundus. In this case, the relationship between the number of zero cross points and the portion having a high reflectance is one in which, the smaller the number of zero cross points is, the shallower the position on the fundus at which the portion having a high reflectance is located is, while the larger the number of zero cross points is, the deeper the position on the fundus at which the portion having a high reflectance is located is. Thus, by converting the number of zero cross points into a luminance value, information on depth position at the portion having a high reflectance is obtained as a luminance value.

In FIG. 3, a portion at which no fundus blood vessel is running is shown in high luminance. At the portion at which no blood vessel is running, the reflectances at the retinal pigment epithelium and the nerve fiber layer are relatively high. Accordingly, the depth corresponding to the intermediate position of the two layers seems to be expressed as a luminance value. This indicates there are portions having a high reflectance both at a shallow position and at a deep position of the retina.

On the other hand, a portion at which a fundus blood vessel is running is shown in low luminance. At the portion at which a fundus blood vessel is running, since the measurement light is blocked by the blood vessel, it does not reach the retinal pigment epithelium. Thus, the reflectance at the nerve fiber layer is relatively high. Accordingly, the depth corresponding to the nerve fiber layer is expressed as a luminance value. This luminance value indicates there is a portion having a high reflectance at a shallow position of the fundus.

Such relationships show that expressing the magnitude of the number of zero cross points in an interference signal at each scanning position as a luminance value can make an image of a running state of fundus blood vessels on the fundus.

In addition, a nipple part of the fundus is shown in higher luminance than other parts. The nipple part is located at a depressed position on the fundus. Hence, at the nipple part, a portion having a high reflectance is located at a deeper position than those at other parts. That is, what is expressed by a luminance value is a depressed state of the nipple. The luminance value expresses the portion having a high reflectance is located at a deeper position than those at other parts.

That is, by expressing the magnitude of the number of zero cross points in an interference signal at each scanning position as a luminance value, it is possible to confirm the morphologic characteristics of the portion of the fundus at the nipple (depressed portion). Also, the number of zero cross points hardly changes even in a case where the light amount of returned light from the fundus is small. Thus, the light amount of returned light has a limited impact on the image.

As described above, with the above method, a favorable image can be obtained from spectral data, which is unsuitable for formation of a front image. Such a fundus image can be used for positioning at the time of obtaining a tomographic image, check of a position of an obtained tomographic image on the fundus, check of a photographing error at the time of obtaining a three-dimensional tomographic image, or the like.

Accordingly, the above method is applicable to an apparatus with no dedicated optical system such as an SLO optical system. This enables significant cost reduction in forming a front image. Naturally, the above method is also applicable to an apparatus with a dedicated SLO optical system. In this case, the above method can be used for check of an error in a three-dimensional tomographic image.

It is to be noted that, in the above setting, a front image is inverted in a case where the optical path length conforming position is located at the rear (back) portion of the fundus. Thus, the height of the luminance of the front image is inverted. This enables determination of whether the front image is a real image or a virtual image.

Hereinafter, a specific example of a method for obtaining a front image by processing spectral data will be described. The control part 70 two-dimensionally scans a rectangular region on the fundus Ef with the measurement light by controlling driving of the scanning driving mechanism 51. The control part 70 then detects spectral power of interference light with respect to each scanning position (X, Y) by the light receiving device 83. Thereby, the control part 70 obtains spectral data $S_{out}$ (k) output from the light receiving device 83.

$S_{out}$ (k) is expressed in the following equation.

$$S_{out}(k) = |E_R(k)|^2 + \sum_n E_R(k)E_S(k)[\exp\{ik(z_R - z_n)\} + \exp\{-ik(z_R - z_n)\}] + |E_S(k)|^2 \quad \text{[Equation 1]}$$

where k is a wavenumber, $E_R$ (k) is an electric field of the reference light, $E_S$ (k) is an electric field of the measurement light, $z_R$ is an optical path length of the reference light, and $z_n$, is an optical path length of the measurement light. It is to be noted that the wavenumber k is a reciprocal of each wavelength obtained by spectral light. The wavenumber k corresponds to each pixel of a line sensor detecting a spectrum. It is to be noted that this is different from the aforementioned wavenumber, which represents the extent of phase lead of an interference signal obtained by the line sensor.

Here, in the signal contained in the spectral data, signal components that are not related to interference components ($1^{St}$ and $3^{rd}$ terms on the right-hand side of Equation (1)) are removed as a noise. Thereby, an interference signal ($2^{nd}$ term on the right-hand side of Equation (1)) corresponding to combined light of the reference light and the measurement light is extracted. For example, to remove the noise, an average (average spectrum) of spectral data at each scanning position is calculated as a noise. Then, the average spectrum as a noise is subtracted from the spectral data $S_{out}$ (k) (so to speak, DC subtraction, refer to FIGS. 4 and 5).

The extracted interference signal is Hilbert-transformed to derive a real part $S_{real}$ (k) and an imaginary part $S_{imag}$ (k) of the interferogram. The Hilbert transformation is a method to obtain an analysis signal (in which a real signal and an imaginary signal are added) from the real signal, regarding a signal obtained by phase-shifting the entire frequency components of the real signal by 90° as the imaginary signal. In the Hilbert transformation, the real part $S_{real}$ (k) and the imaginary part $S_{imag}$ (k) of the interference signal are derived from the obtained analysis signal.

$$S_{real}(k) = 2\sum_n E_R(k)E_S(k)\cos\{k(z_R - z_n)\} \quad \text{[Equation 2]}$$

$$S_{imag}(k) = 2\sum_n E_R(k)E_S(k)\cos\left\{k(z_R - z_n) - \frac{\pi}{2}\right\} \quad \text{[Equation 3]}$$
$$= 2\sum_n E_R(k)E_S(k)\sin\{k(z_R - z_n)\}$$

In this case, the real part $S_{real}$ (k) and the imaginary part $S_{imag}$ (k) can be derived from an analysis signal obtained by Fourier-transforming the interference signal and inverse-Fourier-transforming a signal obtained by nulling virtual image components of the transformed signal (nulling symmetric data). Such processing is substantially the same processing as the Hilbert transformation.

Next, Arc Tangent2 (arc tangent derived by four-quadrant expression), which is a ratio of the derived real part $S_{real}$ (k) and imaginary part $S_{imag}$ (k), is unwrapped. Thereby, a phase signal P (k) is derived. Here, arc tangent, which is a ratio of the real part and imaginary part of the interference signal, is calculated by the Arc Tangent processing. By this processing, data in which phase jumps in a certain period (data in which phase is discontinuous at a zero cross point, at which the signal shifts from a negative to a positive) is obtained. The unwrapping is processing to make the jumping phase, which forms the discontinuity, continuous.

$$P(k) = \text{unwrap}\left[\tan^{-1}\left(\frac{S_{imag}(k)}{S_{real}(k)}\right)\right] \quad \text{[Equation 4]}$$

The phase signal P (k) represents change in phase on each wavenumber k of the interference light. The phase signal P (k) may be used as a signal for deriving the number of zero cross points. For example, the phase signal P (k) represents that the smaller a maximum value max (P) of the phase signal P (k) is, the smaller the number of zero cross points between Kmin and Kmax is. Also, the phase signal P (k) represents that the larger the maximum value max (P) of the phase signal P (k) is, the larger the number of zero cross points between Kmin and Kmax is.

Subsequently, the maximum value max (P) of the phase signal is converted into a luminance value L as a fundus signal F.

$$F = \max(P) \quad \text{[Equation 5]}$$

In this case, a calculating formula, a table or the like in which the maximum value max (P) and the luminance value L correspond to each other is used. For example, the maximum value max (P) is converted into a higher luminance value as it is larger and into a lower luminance value as it is smaller. Then, the luminance value L at each scanning position (X, Y) is arranged to correspond to each pixel as a luminance level at each scanning position (X, Y). Thereby, a front image is formed.

FIG. 3 illustrates an image showing a specific example of a front image formed by the aforementioned method. The front image which is obtained is an image formed based on the number of zero cross points of the interference signal. The luminance L at each scanning position (X, Y) expresses a depth position at a portion having a high reflectance. In this image, a running state of fundus blood vessels, morphologic characteristics of a nipple part, etc. can be checked.

It is to be noted that the phase signal P (k) to be converted into a luminance value L is not limited to a phase signal P (Kmax) with the maximum wavenumber Kmax. A phase signal P (K1) with a certain wavenumber K1 may be converted into a luminance value L. Also, the magnitude of the number of zero cross points has only to be derived from the phase signal P (k). Further, an integral value of the phase signal P (k) may be converted into a luminance value L. This integral value may be an integral value in Kmin to Kmax or an integral value in a certain wavenumber region, for example. Still further, the number of zero cross points may be derived from discontinuous data before unwrapping.

Still further, when an obtained front image is to be output, a raw image or a processed image may be output. For example, in the image processing, the luminance value L may be divided into plural levels (for example, 7 levels), and a color image corresponding to the respective levels may be displayed. Also, an image obtained through certain filtering may be output.

FIG. 5 illustrates a flowchart showing a second embodiment of the invention. A method in the second embodiment is one in which the number of zero cross points of an interference signal is derived directly without deriving a real part and an imaginary part of the interference signal.

An interference signal part $S_{real}(k)$ extracted by denoising is binarized based on whether the signal is positive or negative (binarization processing). For example, a region in which the signal is lower than a threshold value 0 is converted into 0 while a region in which the signal is the threshold value 0 or higher is converted into 1.

$$S_{binary}(k) = \begin{cases} 1 & S_{real}(k) \geq 0 \\ 0 & S_{real}(k) < 0 \end{cases} \quad \text{[Equation 6]}$$

Subsequently, the binarized interference signal is differentiated.

$$S_{diff1}(k) = \frac{d}{dk}(S_{binary}(k)) \quad \text{[Equation 7]}$$

Subsequently, the differentiated interference signal is further binarized based on whether the signal is positive or negative. For example, a region in which the signal is lower than a threshold value 0 is converted into 0 while a region in which the signal is the threshold value 0 or higher is converted into 1.

$$S_{diff2}(k) = \begin{cases} 1 & S_{diff1}(k) \geq 0 \\ 0 & S_{diff1}(k) < 0 \end{cases} \quad \text{[Equation 8]}$$

The respective signal 1 portions in the differentiated and binarized interference signal represent points each of whose corresponding phase has led 360°. The number of signal 1 portions is counted to find the number of zero cross points between Kmin and Kmax.

This integral value (the number of zero cross points) is converted into a luminance value L as a fundus signal F.

$$F = \Sigma S_{diff2}(k) \quad \text{[Equation 9]}$$

In this conversion, a calculating formula, a table or the like in which the fundus signal F and the luminance value L correspond to each other is used. For example, the number of zero cross points is converted into a higher luminance value as it is larger and into a lower luminance value as it is smaller. Then, the luminance value L at each scanning position (X, Y) is arranged to correspond to each pixel as a luminance level at each scanning position (X, Y). Thereby, a front image is formed. By this method as well, an image similar to one in FIG. 3 is obtained.

It is to be noted that a method for deriving the number of zero cross points directly is not limited to the above method as long as it is a method for detecting zero cross points intersecting with a reference line by using it in the interference signal. For example, the number of portions having a value 0 in the interference signal on wavenumber k may be counted.

Meanwhile, to detect the number of zero cross points, zero cross points may be detected in advance, and the number of peaks between the detected zero cross points may be detected. Alternatively, only zero cross points when the interference signal shifts from a negative to a positive or only zero cross points when the interference signal shifts from a positive to a negative may be detected. Naturally, both the zero cross points may be detected, and their number may be derived.

Also, the number of zero cross points may be detected from the spectrum before denoising. For example, raw data of the spectral data and an average of the spectral data at respective scanning positions may be compared, and the number of cross points of these may be detected.

Also, an average of lengths between detected zero cross points may be derived. The reason for this is that an average period of waveforms sectioned by zero cross points tends to be short when the number of zero cross points is large while the average period of waveforms sectioned by zero cross points tends to be long when the number of zero cross points is small. Meanwhile, when the interference signal has a waveform similar to a sine wave, a period of an interference signal that changes approximately sinusoidally with respect to wavenumber k may be detected.

In the foregoing description, information on depth position at a portion having a high reflectance is obtained from an interference signal before obtaining a depth profile. However, information on depth position may be obtained by use of a depth profile obtained from an interference signal. For example, after acquisition of a tomographic image, a point showing the maximum luminance per A scan signal is detected, and the depth position of the point is output as a luminance value. In this case, the position showing the maximum luminance is expressed as lower luminance as it is shallower and as higher luminance as it is deeper, for example.

Figure 6:
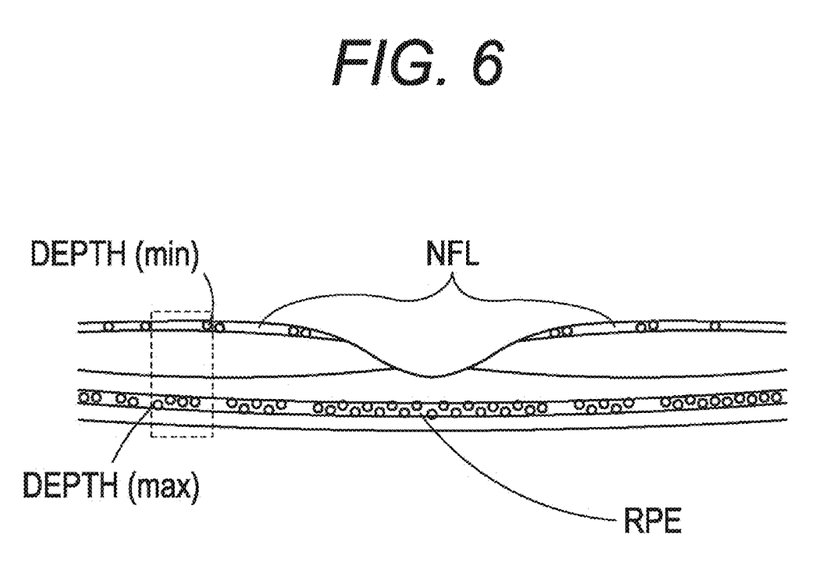
FIG. 6 illustrates an example in a case of obtaining information on depth position by use of a depth profile obtained from the interference signal.

An image having two portions (nerve fiber layer and pigment epithelium) showing high luminance in the depth direction, such as a fundus image, may be treated as follows. When a depth position showing the maximum luminance at a certain pixel is to be detected, a depth position of a luminance point located at the shallowest position (or the deepest position) among respective highest luminance points in an A scan signal corresponding to the pixel and A scan signals corresponding to plural pixels (for example, 5 pixels) adjacent to the pixel may be detected (refer to FIG. 6).

The aspect of the invention may be applied to an ophthalmic photographing apparatus as long as it is an ophthalmic photographing apparatus having an interference optical system receiving interference light obtained by combining measurement light from an examinee's eye with reference light and photographing a tomographic image of a predetermined portion of the examinee's eye (for example, tomographic image of an anterior segment).

With the above method, an image is formed based on the number of zero cross points. Accordingly, this method is not much influenced by supersaturation of an amplitude level of a spectrum. For example, in a case where a front image of an anterior segment is to be obtained, the image is not influenced by strong noise reflected light detected at a top portion of a cornea, and morphologic characteristics of the anterior segment can be obtained.

The aspect of the invention is not applied only to an ophthalmic photographing apparatus. The aspect of the invention may be applied to an optical tomographic image photographing apparatus photographing a tomographic image of a living body other than an eye (for example, skin or a blood vessel), a sample other than a living body or the like. Naturally, an object is not limited to a living body.

<Differentiation of Interference Signal>

When obtaining a front image, noise components may be eliminated from the front image by adding a differentiation process (high-pass filter) of the interference signal and detecting the zero cross points from the differentiated interference signal.

<Frequency Conversion of Interference Signal>

The image quality of a front image can be enhanced by converting the frequency of the interference signal and obtaining the front image based on the number of zero cross points in the converted interference signal. In general, in frequency conversion, when $e^{ikz}$ is an interference signal and $\Delta z$ is a frequency shift amount, $e^{ikz}$ and $e^{ik\Delta z}$ are multiplied to shift the frequency of the interference signal.

$$e^{ikz} \cdot e^{ik\Delta z} = e^{ik(z+\Delta z)} \quad \text{[Equation 10]}$$

Figure 7:
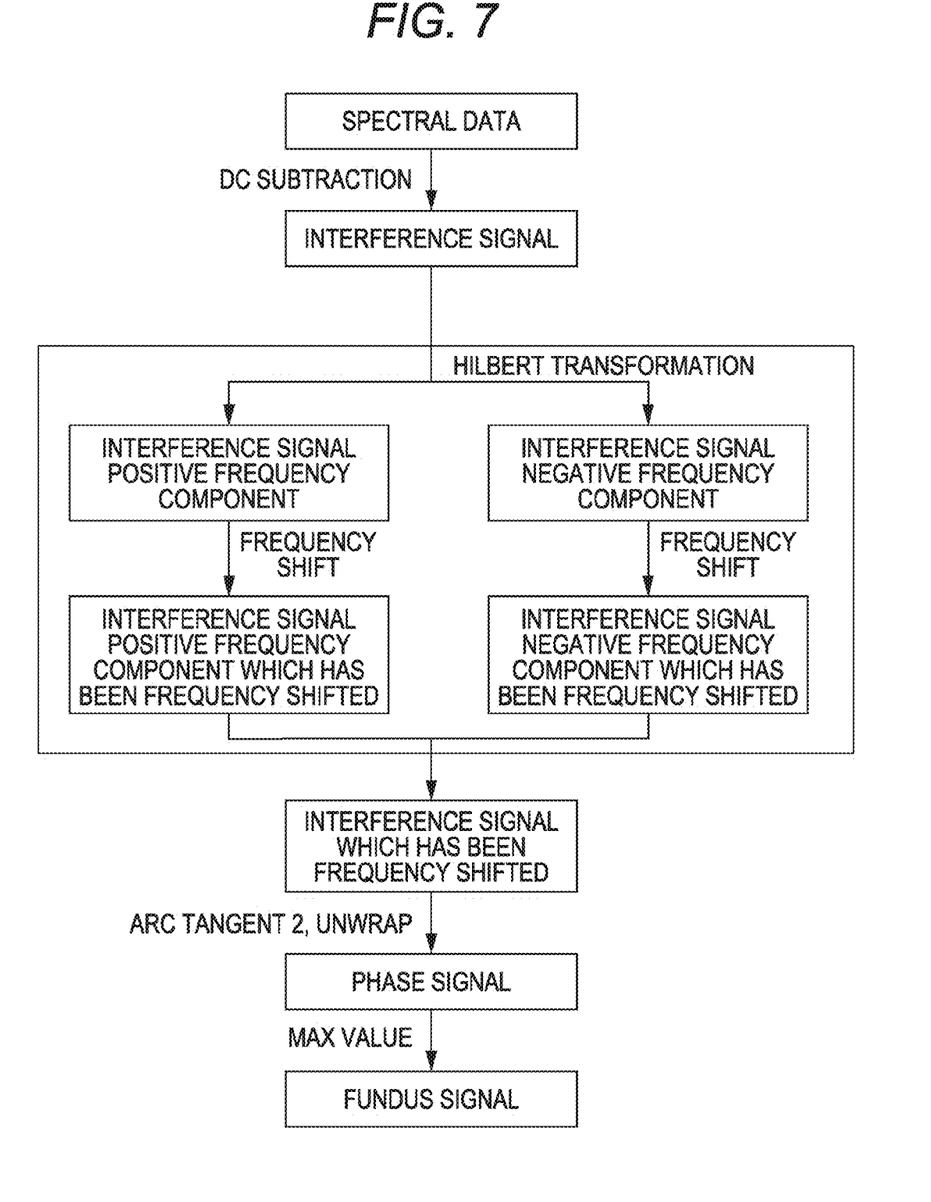
FIG. 7 is a flowchart illustrating an example of obtaining a front image upon conversion.

FIG. 7 is a flowchart illustrating an example of obtaining a front image upon conversion. For example, the extracted interference signal is subjected to Hilbert transformation. As a result, a positive frequency component and a negative frequency component of the interference signal are derived. Using these components, a frequency shift corresponding to $\Delta z$ is carried out.

For example, $e^{i\Delta z}$ is multiplied by the positive frequency component $S_{real}(k)+iS_{imag}(k)$.

$$S_{real}(k) + iS_{imag}(k) = E_R(k)E_S(k)\sum_n e^{ik(Z_R-Z_n)} \cdot e^{ik\Delta z} \quad \text{[Equation 11]}$$

On the other hand, $e^{-i\Delta z}$ is multiplied by the negative frequency component $S_{real}(k)-iS_{imag}(k)$.

$$S_{real}(k) - iS_{imag}(k) = E_R(k)E_S(k)\sum_n e^{-ik(Z_R-Z_n)} \cdot e^{-ik\Delta z} \quad \text{[Equation 12]}$$

At this time, the frequency within the interference signal may be changed before Hilbert transformation.

Subsequently, a phase signal P (k) is found by combining the positive frequency component and the negative frequency component. The maximum value max (P) of the phase signal is converted into a luminance value L as a fundus signal F. The fundus signal F is arranged as a luminance at each XY position to be formed as a front image. For example, among the max (P) obtained at each XY position, the minimum value of the max (P) is expressed by a luminance 0, whereas the maximum value of max (P) is expressed by a luminance 255. Meanwhile, the positive frequency component and the negative frequency component of the interference signal are not necessarily to be combined. The phase signal P (k) may be found by using any one of the positive frequency component and the negative frequency component after Hilbert transformation.

An example of control using conversion will now be explained. When a fundus tomographic image is obtained, the fundus position changes relative to an optical path length conforming position S (position corresponding to an optical path length of the reference light) resulted from slight motion of the fundus by breathing or movement of the entire eye or the like (refer to FIGS. 8A and 8B). Therefore, the number of zero cross points obtained at each point also changes. Thus, if the fundus position changes, there is a possibility that the image quality (for example, contrast or brightness) of the front image will differ even if the image is at the same position on an identical eye.

Figure 8A:
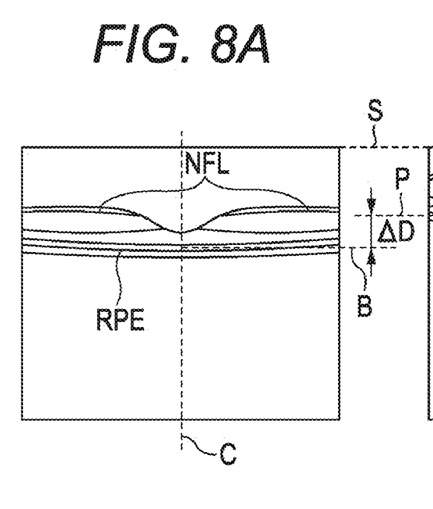
FIGS. 8A and 8B illustrate tomographic images when a fundus position corresponding to an optical path length conforming position S (position corresponding to an optical path length of the reference light) changes.
Figure 8B:
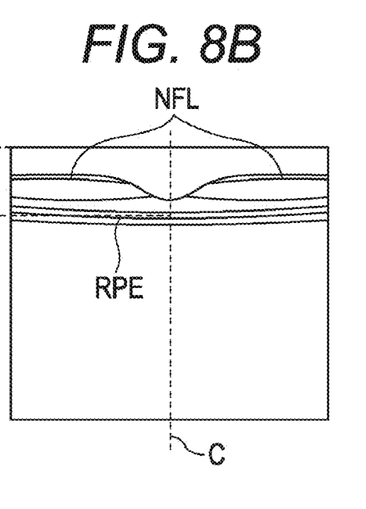

The control part 70 detects a position in the depth direction at which the tomographic image is obtained. The control part 70 then shifts the frequency of the interference signal based on the detected position information. Thereby, the control part 70 stabilizes the image quality of the front image.

The control part 70 detects a positional aberration of the tomographic image in the depth direction based on the obtained tomographic image. Based on the detection result, the control part 70 multiplies $e^{i\Delta z}$ by the interference signal $e^{ikz}$ so that the frequency of the interference signal from a predetermined area of the fundus (for example, RPE (retinal pigment epithelium)) is converted into a predetermined frequency. As the predetermined frequency, for example, a frequency of the interference signal is set such that an image of a predetermined area is obtained at a reference position B which is separated from the conforming position S by only a certain distance.

In general, if a tomographic image is obtained based on an interference signal which has been frequency shifted, the control part 70 shifts the frequency of the interference signal so that the predetermined area in the tomographic image is formed at the reference position B.

For example, the control part 70 obtains a luminance distribution (luminance distribution at a center part C) of the tomographic image in the depth direction, and then detects the aberration amount $\Delta D$ between a peak position (corresponding to RPE) and the reference position B based on the luminance distribution. The control part 70 then obtains a frequency shift amount $\Delta z$ corresponding to the detected aberration amount $\Delta D$, and shifts the frequency of the interference signal $e^{ikz}$.

In this case, the necessary frequency shift amounts $\Delta z$ corresponding to each aberration amount $\Delta D$ are calculated beforehand by simulation or experimentation or the like, and stored in a memory 72 as correction information (for example, a correction table, a correction formula, and the like). In this case, the positive and negative signs of the shift amount change depending on the aberration direction.

The control part 70 sequentially converts the frequency of the interference signals obtained at each XY position, and obtains a front image based on the converted interference signals. Thereby, even if the position in the depth direction at which the tomographic image is obtained changes, a stable front image can be obtained.

The above-described process is also useful when adjusting the optical path length in accordance with the ocular axial length. In addition, the above-described process is also useful in a device which carries out EDI (enhanced depth imaging) as well as normal imaging. In this case, for example, the control part 70 detects the positional aberration amount $\Delta D$ of the tomographic image when the fundus is positioned in front of and behind the conforming position S. The control part 70 then obtains the frequency shift amount $\Delta z$ corresponding to the detected aberration amount $\Delta D$, and then shifts the frequency of the interference signal $e^{ikz}$ using $\Delta z$. Thereby, inversion of the luminance can be avoided.

In the above explanation, by shifting the frequency of the interference signal, luminance changes in the front image caused by changes in the position at which the tomographic image is obtained are corrected. However, the correction method is not limited to that described above. In general, the control part 70 detects the position in the depth direction at which the tomographic image is obtained based on an output signal from a spectral detecting unit. The control part 70 then corrects luminance changes in the front image caused by changes in the position at which the tomographic image is obtained based on the detected position information.

For example, it is also possible to correct the maximum value max (P) of the phase signal or the luminance value L based on the aberration amount ΔD. The relationship between the amount of change of a measured value (for example, the maximum value max (P), the luminance value L) when an image is obtained at an offset position relative to the reference position and the aberration amount ΔD is used as the correction information.

The interference signal and the position at which the tomographic image is obtained are in a fixed relationship. Therefore, the control part 70 may also indirectly obtain a change in the position at which the tomographic image is obtained using the interference signal. In this case, the control part 70 uses the obtained result to correct luminance changes in the front image caused by changes in the position at which the tomographic image is obtained. For example, if the number of zero cross points in the interference signal drops below an allowable range, the control part 70 makes corrections in accordance with the amount of change in the number of zero cross points obtained from the reference position relative to the number of measured zero cross points.

<Shift to the High Frequency Side>

Figure 9A:
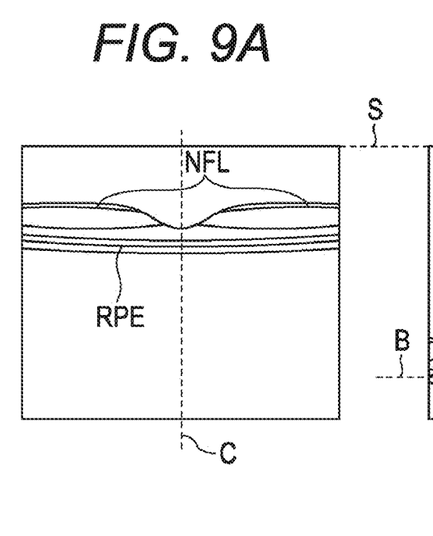
FIGS. 9A and 9B illustrate explanatory diagrams of a shift to the high frequency side.
Figure 9B:
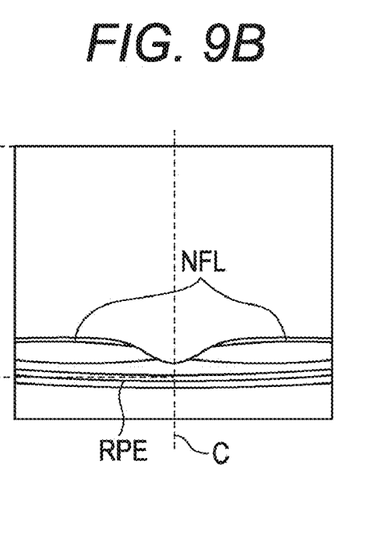

In the above-described conversion process, it is preferable to set the position in the depth direction at which the tomographic image is obtained close to the conforming position S in order to increase the S/N ratio of the tomographic image (refer to FIG. 9A). On the other hand, it is preferable to set the reference position B in the depth direction for obtaining the front image at a position far from the conforming position S in order to increase the S/N ratio of the front image (refer to FIG. 9B).

The control part 70 controls the driving of the reference mirror driving mechanism 50 so that the tomographic image is obtained near the conforming position S (refer to FIG. 9A). The interference signal at an optical path length (position at which the tomographic image is normally obtained) such that the fundus is arranged close to the conforming position S has a low frequency. Thus, the control part 70 converts the frequency of the interference signal to a high frequency and obtains the front image using the zero cross points of the converted interference signal.

For example, the control part 70 multiplies the interference signal $e^{ikz}$ by $e^{i\Delta z}$ so that the frequency of the interference signal obtained from a predetermined area of the fundus (for example, RPE) is converted to a predetermined frequency set to fall within a frequency band that is higher than the frequency when the interference signal is extracted from the spectral.

The predetermined frequency is normally set so that, for example, it is higher than a frequency of the above described interference signal obtained after completion of automatic OPL (optical path length) adjustment. Preferably, the predetermined frequency is set to a frequency of an interference signal obtained when the tomographic image is obtained close to a limit position (forward or rearward) of an imagable range in the depth direction (refer to FIG. 9A).

Figure 10A:
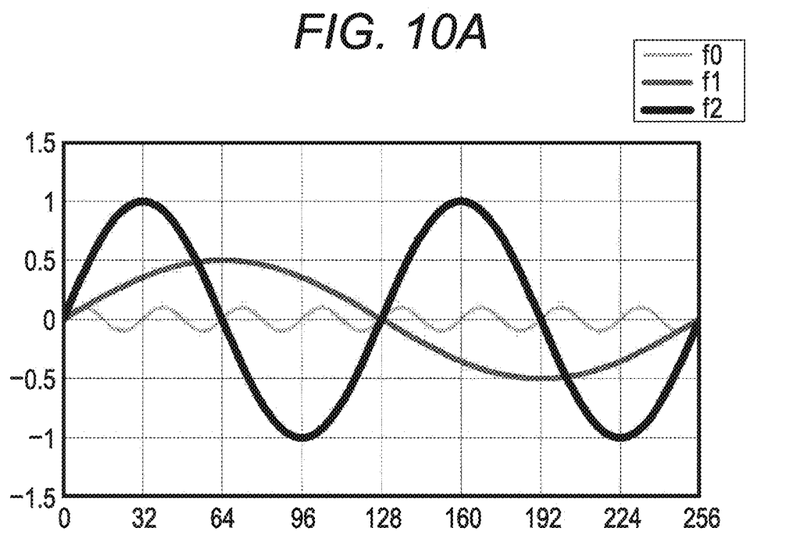
FIG. 10A and FIG. 10B simply illustrate an interference signal before frequency shift.
Figure 10B:
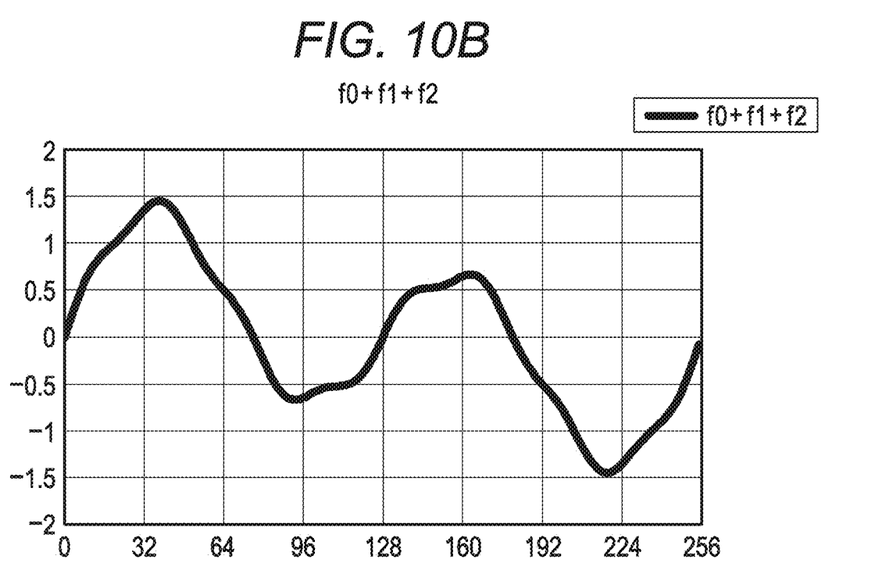
Figure 11A:
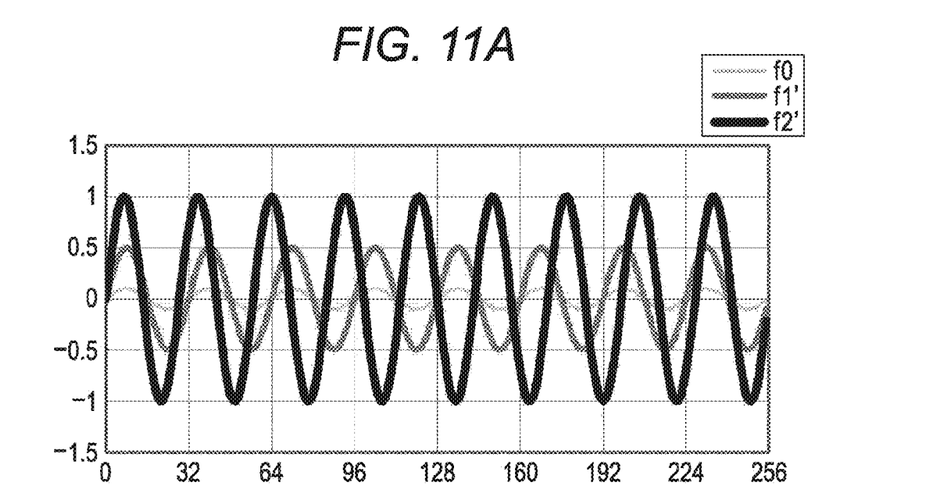
FIG. 11A and FIG. 11B simply illustrate an interference signal after the frequency has been shifted.
Figure 11B:
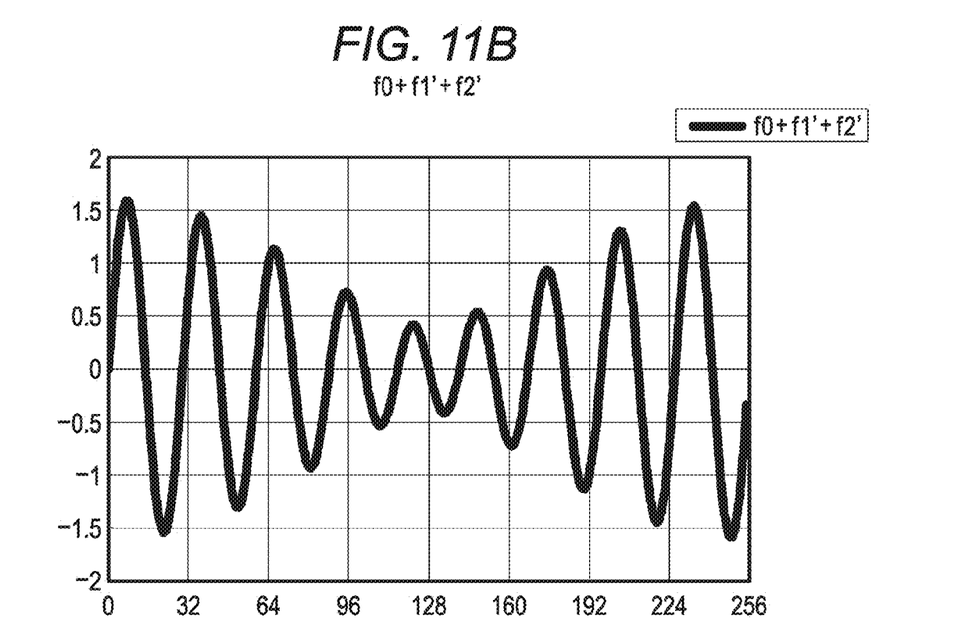

In this way, the control part 70 converts the frequency of the interference signal such that the frequency increases (the phase-lead becomes faster). FIGS. 10A and 10B simply illustrate the interference signal before frequency shift. FIGS. 11A and 11B simply illustrate the interference signal after the frequency has been shifted. The horizontal axis (0 to 256) in these figures represents a signal received at a part of a line sensor. The vertical axis represents the amplitude.

In FIGS. 10A and 11A, the waveform f0 corresponds to high frequency noise (noise component remaining in the interference signal), the waveform f1 corresponds to light from an NFL (nerve fiber layer), and the waveform f2 corresponds to light from an RPE (retinal pigment epithelium), respectively. The waveforms shown in FIGS. 10B and 11B are combined waveforms in which the waveforms f0, f1, and f2 are superposed. Generally, the degree of reflection at the RPE is larger than the degree of reflection at the NFL. When macroscopically viewing the interference signal (refer to the combined waveform), if there is no running of the blood vessels, the reflection at the RPE is the strongest, and the reflection at the NFL is the second largest.

<Before Frequency Shift>

In FIG. 10A, in the waveforms f1 and f2, the phase lead is slow. As shown in FIG. 10B, in the combined waveform, the inclination is small (gradual). Therefore, the combined waveform is heavily influenced by high frequency noise. Thus, the position of the zero cross points changes more with respect to the waveform f2. Further, the shape of the waveform itself is greatly distorted. In this kind of case, noise occurs easily in the front image that is formed.

If an attempt is made to obtain the two-dimensional distribution of the depth position of the RPE in the XY directions as the front image, the result is that a two-dimensional distribution at a depth position in between the NFL and the RPE is obtained.

<After Frequency Shift>

In FIG. 11A, in the waveforms f1 and f2 which have been shifted to a higher frequency, the phase lead is fast. As shown in FIG. 11B, in the combined waveform, the inclination is large (steep). Therefore, the combined waveform is not heavily influenced by high frequency noise. The position of the zero cross points does not change much with respect to the waveform f2. Further, the shape of the waveform itself does not change much. In this kind of case, a stable front image with little influence from noise is obtained.

Compared to the image before frequency shift, as a result of frequency shift, the two-dimensional distribution of the depth position close to the RPE in the XY directions is obtained as the front image. In addition, although it depends on the object, the front image at a depth position in an area where the reflection is strong is obtained with high accuracy.

In the above-described conversion process, conversely, the frequency may also be shifted so that the frequency of the interference signal decreases, and then a front image may be obtained based on the shifted interference signal.

While the invention has been illustrated and described in detail, the foregoing description is in all aspects illustrative and not restrictive. It is therefore understood that numerous modifications and variations can be devised without departing from the spirit and scope of the invention.

What is claimed is:

1. An apparatus for generating a two-dimensional image of an object, comprising:
   an optical coherence tomography (OCT) optical system including:
   a light source for emitting light;
   a splitter for splitting the light emitted from the light source into measurement light guided to a measurement optical path and reference light guided to a reference optical path;
   a scanner that is arranged in the measurement optical path for scanning the object in at least one of X and Y directions with the measurement light; and
   a detector configured to detect a spectrum of interference light of the measurement light from the measurement optical path reflected on the object and the reference light from the reference optical path at each of X and Y scanning positions of the measurement light on the object; and a processor configured to obtain a phase change of an interference signal contained in the spectrum at each of the X and Y scanning positions and to generate a two-dimensional image representing, in the X and Y directions, a depth position, in a depth direction, of a portion of the object where reflection is strong.

2. The apparatus according to claim 1, wherein the object is an eye.

3. The apparatus according to claim 1, wherein the detector includes any one of a spectrometer for splitting the interference light and a wavelength swept source.

4. The apparatus according to claim 1, wherein the processor detects a position in a depth direction at which a tomographic image is obtained based on an output signal from the detector, and corrects luminance changes in a front image caused by changes in the position at which the tomographic image is obtained based on the detected position.

5. The apparatus according to claim 2, wherein the object is a fundus.

6. The apparatus according to claim 1, wherein the processor is configured to generate the two-dimensional image of the object by detecting a number of zero cross points of the interference signal from the phase change and converting the number of the zero cross points of the interference signal into a luminance value at each of the X and Y positions.

7. The apparatus according to claim 6, wherein the processor Hilbert-transforms the interference signal to obtain an analysis signal in which a real signal and an imaginary signal of the interference signal are added, obtains a phase signal representing the phase change of the interference signal of the interference light of each wavelength based on the analysis signal, detects the number of the zero cross points of the interference signal based on the phase signal, and converts the number of the zero cross points of the interference signal into the luminance value at each of the X and Y positions.

8. The apparatus according to claim 6, wherein the processor directly detects the number of the zero cross points of the interference signal from a real signal of the interference signal and converts the number of the zero cross points of the interference signal into the luminance value at each of the X and Y positions.

9. The apparatus according to claim 6, wherein the processor converts a frequency of the interference signal, detects the number of the zero cross points of the interference signal having the converted frequency, and obtains the two-dimensional image in the X and Y directions of the object based on the number of zero cross points of the interference signal.

10. The apparatus according to claim 9, wherein the processor converts the frequency of the interference signal such that the frequency increases.

11. The apparatus according to claim 9, wherein the processor converts the frequency of the interference signal such that the frequency falls within a predetermined frequency band set higher than the frequency.

* * * * *